United States Patent [19]
Adair

[11] Patent Number: 5,812,188
[45] Date of Patent: Sep. 22, 1998

[54] STERILE ENCAPSULATED ENDOSCOPIC VIDEO MONITOR

[76] Inventor: Edwin L. Adair, 317 Paragon Way, Castle Pine Village, Colo. 80104

[21] Appl. No.: 678,811

[22] Filed: Jul. 12, 1996

[51] Int. Cl.$^6$ .............................. H04N 7/18; B65D 85/86
[52] U.S. Cl. .......................... 348/77; 600/101; 128/849; 174/17.05; 206/438; 206/320
[58] Field of Search ...................................... 600/121, 122, 600/101, 102, 133; 128/849, 851, 852, 847, 853; 206/210, 334, 438, 466, 305, 576, 829, 320, 524–8; 348/840, 836, 143, 373, 77, 82; 174/17.05; 200/302.2; 150/154, 165; 396/25, 534; 383/106, 121.1, 68

[56] References Cited

U.S. PATENT DOCUMENTS

| | | | |
|---|---|---|---|
| 1,535,312 | 4/1925 | Hosking | 396/27 |
| 3,162,107 | 12/1964 | Byers | 396/27 |
| 3,929,178 | 12/1975 | Hickey | 206/524.8 |
| 4,155,453 | 5/1979 | Ono | 396/27 |
| 4,275,719 | 6/1981 | Mayer | 128/849 |
| 4,621,735 | 11/1986 | Coon et al. | 206/438 |
| 4,963,693 | 10/1990 | Kodl | 206/305 |
| 5,020,546 | 6/1991 | Russo | 128/849 |
| 5,080,155 | 1/1992 | Crozier | 174/17.05 |
| 5,316,541 | 5/1994 | Fischer | 128/849 |
| 5,332,095 | 7/1994 | Wu | 206/524.8 |
| 5,363,838 | 11/1994 | George | 600/109 |
| 5,429,142 | 7/1995 | Szabo et al. | 128/849 |

FOREIGN PATENT DOCUMENTS

WO 89/04629  6/1989  Germany.

OTHER PUBLICATIONS

Sharp Corporation, *Color Display Modules*, Jan., 1995, pp. 1–13.
Sony Corporation, *8.6" LCD Monitor Module, SEU–2902*, pp. 1–2.
Sony Corporation, *10.4" LCD Monitor Module, LMD–1040XC*, pp. 1–2.

*Primary Examiner*—John P. Leubecker
*Attorney, Agent, or Firm*—Fields and Johnson, P.C.

[57] ABSTRACT

A sterile enclosure is provided having a body portion for encapsulating one or more video monitors used for viewing one or more surgical areas in a sterile operating field. The enclosure may be flexible or rigid and have one or more cable drapes extending from the body to cover one or more cables associated with the video monitor. In some embodiments, the body is flexible. In another embodiment, the body is rigid. The body is transparent in at least an area for viewing the screen of the video monitor and is substantially impervious to liquid and gas. A vacuum line may be connected to the body portion to evacuate air therefrom.

11 Claims, 4 Drawing Sheets

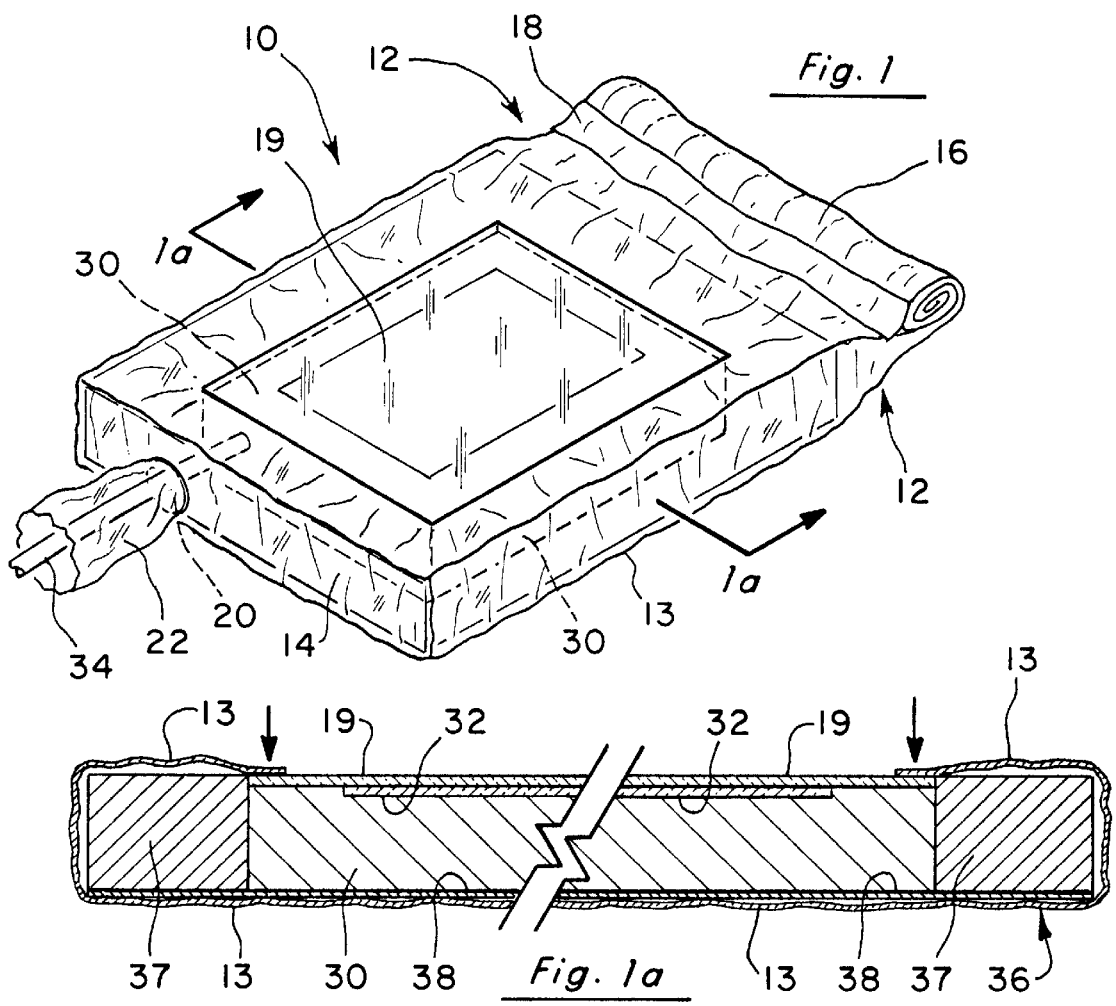
Fig. 1
Fig. 1a
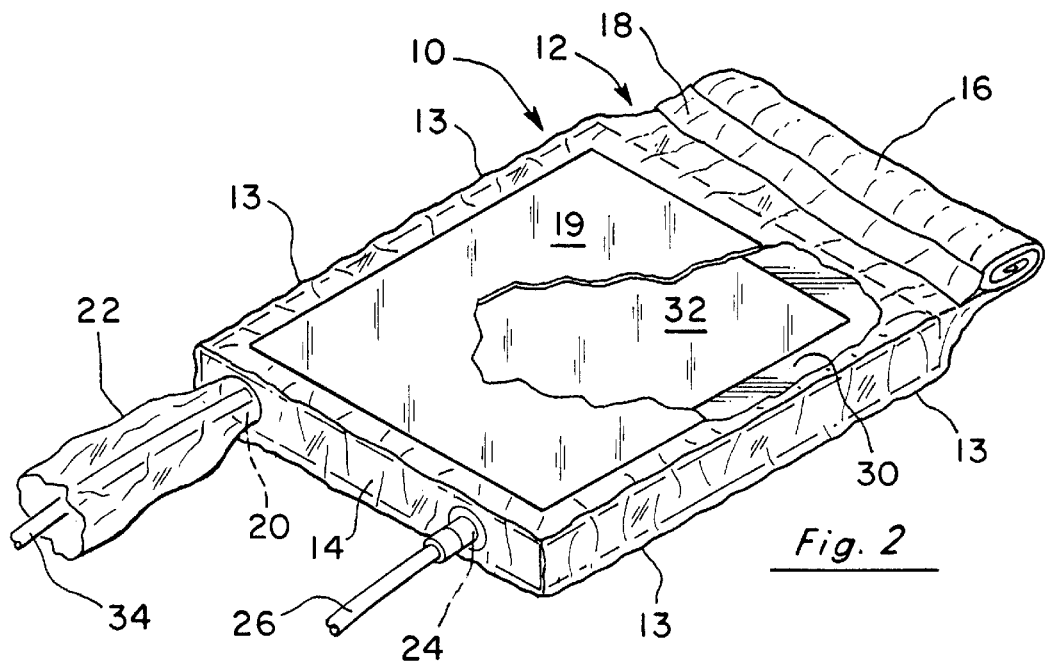
Fig. 2

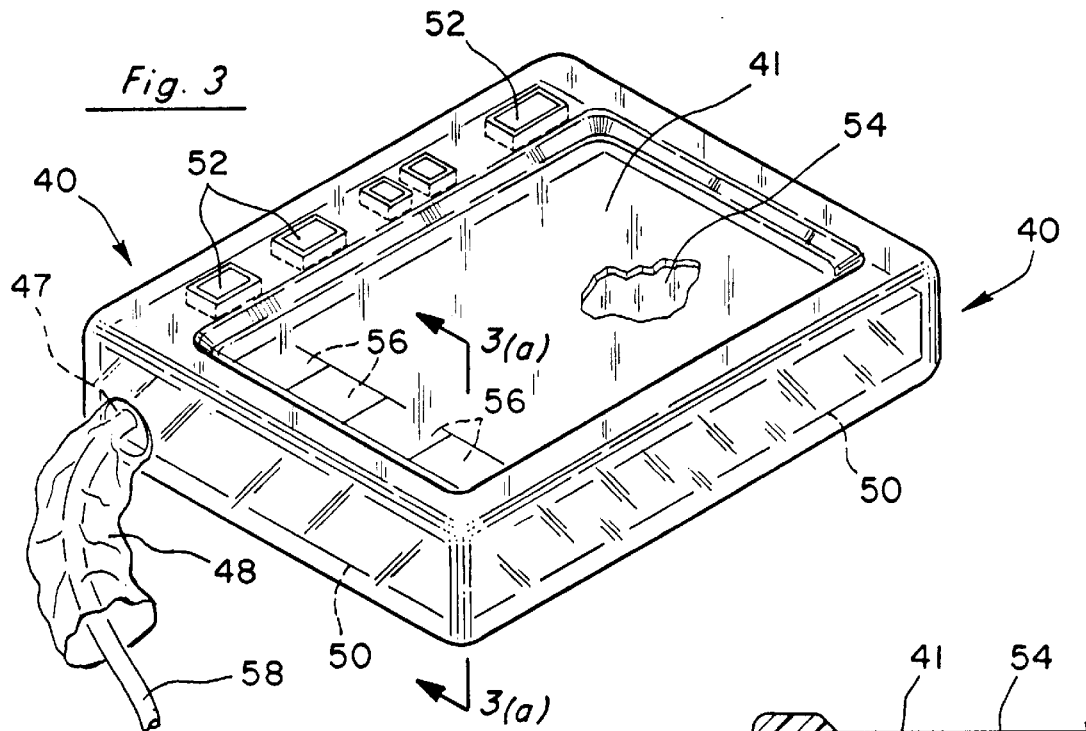
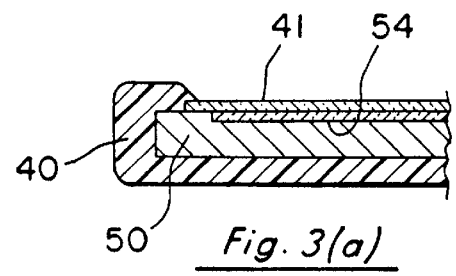
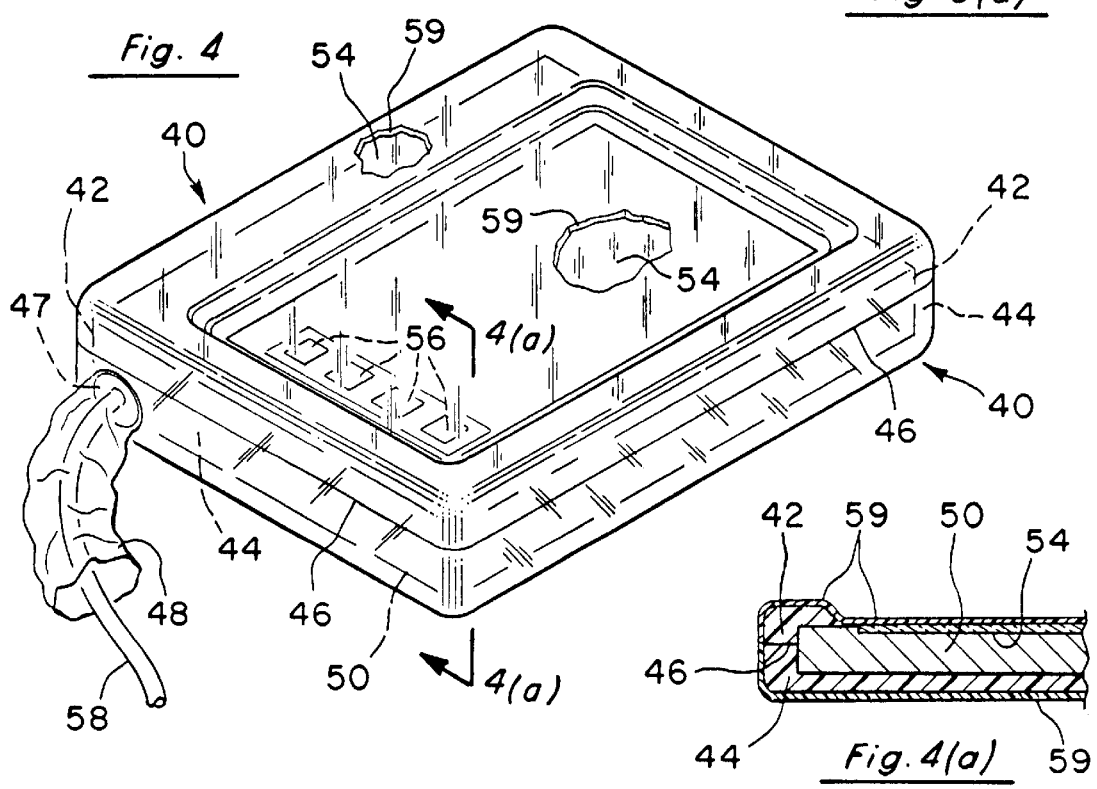
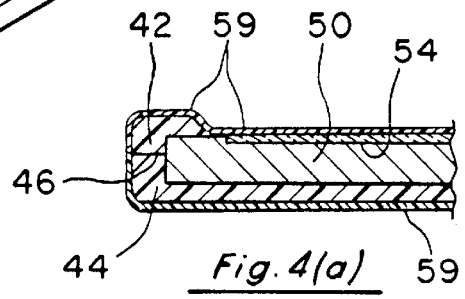

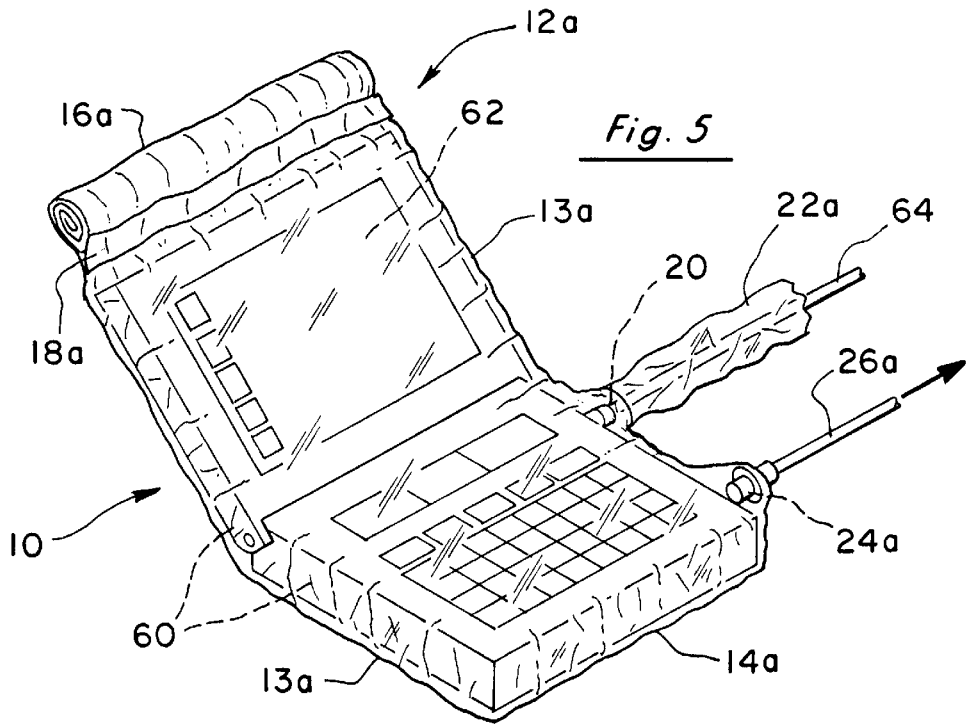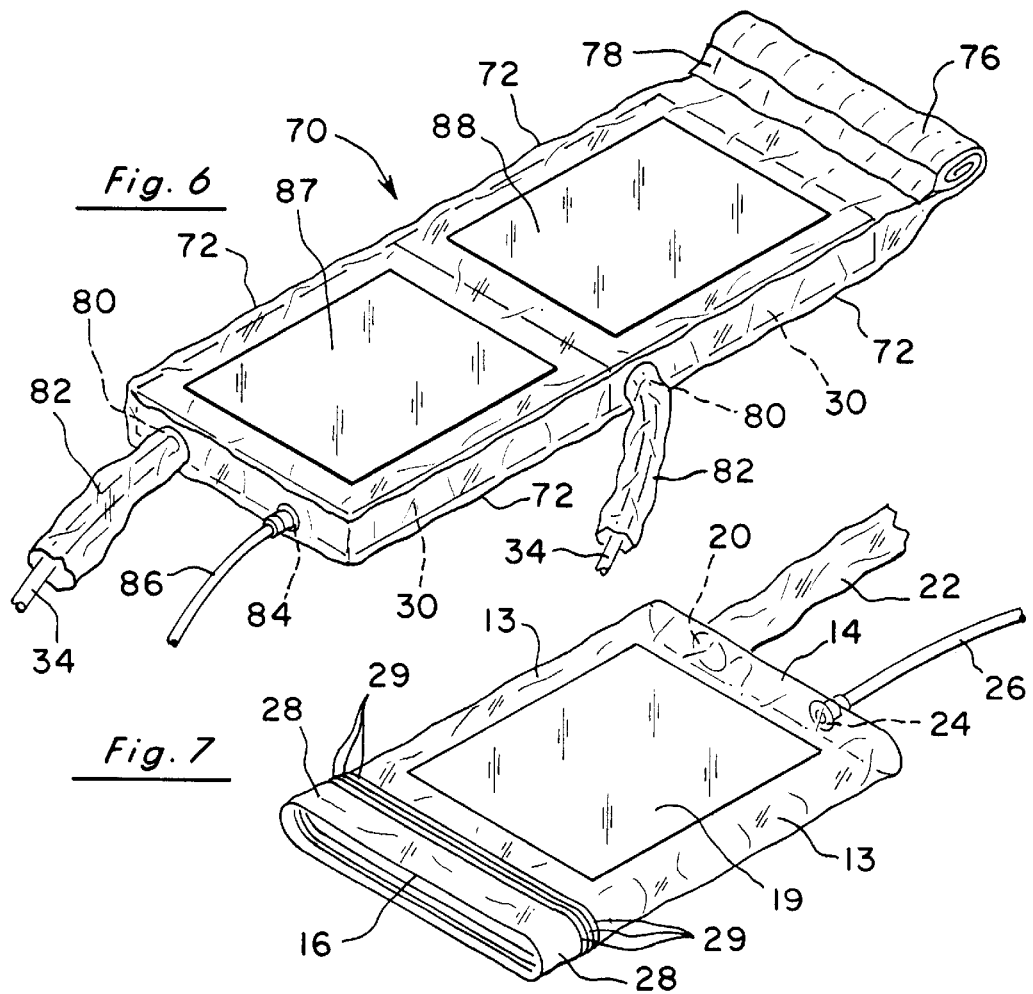

STERILE ENCAPSULATED ENDOSCOPIC VIDEO MONITOR

TECHNICAL FIELD

This invention relates to an apparatus and method which provides a visual display of a surgical site and more particularly to a sterile encapsulated endoscopic video monitor and method used in conjunction with an endoscopic camera and instrument to provide an image of a surgical area within the sterile field of an operating room.

BACKGROUND ART

Endoscopic procedures have become the standard in modern medicine for conducting surgical procedures which are minimally invasive. Prior to the development of endoscopic procedures, surgery required direct visual access to the surgical area which oftentimes resulted in extreme trauma to the patient due to large incisions and the like. With the development of endoscopic instruments which include video cameras that can transmit an image of the surgical site to a video display, surgical procedures can be conducted in a less invasive manner. Although endoscopic procedures represent a great leap forward in terms of minimizing patient trauma, endoscopic procedures using video displays have also resulted in new problems.

One prerequisite for successful endoscopic procedures is that the surgeon must be skilled with the use of the endoscope so that the endoscope itself does not cause unnecessary damage to the patient's tissues. In most endoscopic procedures conducted today, the surgeon may view a standard television (TV) monitor or video screen which displays an image of the surgical site as photographed by a video camera positioned within or adjacent the endoscopic instrument. One problem created by the use of endoscopes with integral video cameras is that the surgeon must be able to precisely manipulate the endoscope within the patient's body while looking away from the patient and toward the remote TV monitor. Since the standard TV monitor must be placed at a location substantially remote from the patient's body, surgeons have had to develop particular dexterity and skill in ensuring that the endoscope does not unintentionally damage body tissues during the surgical procedure.

Another problem associated with endoscopic procedures utilizing TV monitors or video screens is that the surgeon is dependent upon another person to control the exact type of image displayed on the TV monitor. More particularly, the surgeon may be able to adjust the focus of the image by a dial located upon the endoscope; however, neither the endoscope nor the camera attached to the endoscope have controls to vary the brightness, contrast or magnification of the image. Accordingly, the surgeon must direct operating room personnel to adjust the visual display as desired.

Another problem associated with the advent of endoscopic procedures utilizing video equipment is that since additional equipment is brought into the operating room, there is a concern for preventing contamination by the equipment of the sterile field of the operating room. Since TV monitors and other electronic equipment tend to naturally induce or create an electric charge, dust containing microbes tends to collect on this equipment wherein such microbes can then be transmitted to the sterile operating field of the operating room. It has been found that a surgeon placing his hand near a TV monitor displaying an image of the surgical area can attract undesirable microbes via the differential in electrostatic charge between the surgeon's hand and the TV or monitor screen.

Additionally, standard TV monitors and their associated controls are typically large and heavy and difficult to manipulate within the operating room. Accordingly, this equipment cannot be placed directly adjacent to the patient to enhance the surgeon's ability to manipulate the endoscopic instrument in a visually aligned position.

Each of the above-identified disadvantages of current endoscopic procedures utilizing standard video equipment is overcome by the invention claimed herein.

DISCLOSURE OF THE INVENTION

According to the present invention, a sterile encapsulated endoscopic video monitor and method are provided. According to the first embodiment of the invention, a sterile enclosure is provided for encapsulating a video monitor or monitor module. As used herein, the term "video monitor" refers to all devices which can provide a visual image to include standard TV monitors and monitor modules which are much lighter in weight than TV monitors and which have much smaller profiles in terms of depth or thickness. Examples of monitor modules available are those manufactured Sony, known as "LCD Monitor Modules," which have particularly thin bodies and are lightweight. For example, Model No. SCU-2092, manufactured by Sony, is a chassis-type LCD monitor module having a 58 mm depth and weighing less 2,000 gms. In addition to Sony, there are other manufacturers of similar monitor modules in terms of weight and depth or thickness such as Texas Instruments, Xerox and Sharp. For each of these monitor modules, they are self-contained units in that the monitor modules require, at most, a single communication cable, which communicates with a video camera and a power cable. Some manufacturers make monitor modules which require no communication or power cables and communicate with a video camera system by means of infrared, radio or other electromagnetic signals. Also, these monitor modules may be powered by their own internal power source. Thus, it shall be understood that the monitor modules described herein do not necessarily require any communication cables or power cables in order to produce an image of the surgical site. The sterile enclosure includes a flexible body which is adaptable to receive video monitors or monitor modules of varying shapes and sizes. The open proximal end of the sterile enclosure may be sealed for completely enclosing the monitor module therein. One or more ports may be formed on the flexible body of the sterile enclosure enabling cables or other communication structures to exit the sterile enclosure for communication with other video equipment within the operating room. A corresponding cable drape is provided at each of the ports to ensure that any cables which may exit the sterile enclosure are isolated from the sterile field of the operating room. The sterile enclosure may be made of a homogeneous material which is substantially transparent so that the monitor screen of the monitor module may be easily viewed during a surgical procedure in a sterile encapsulated state. Alternatively, a separate window portion may be formed on the sterile enclosure which is made of a different material than the flexible body portion and which enhances the ability to view the monitor screen of the monitor module. For example, the sterile enclosure may be made of styrene, polycarbonate, or polyethylene and the window portion may be made of acrylic. The sterile enclosure is substantially liquid and gas impermeable to prevent contaminants from the encapsulated monitor module migrating into the sterile field of the operating room.

A vacuum port may be formed on the flexible body of the sterile enclosure, and communicates with a source of vacuum external to the monitor module for pulling a vacuum on the interior open space within the sterile enclosure which covers the monitor module and associated cable(s).

In another embodiment, the sterile endoscopic encapsulated video monitor of this invention may include a rigid or semi-rigid monitor module frame which encloses the video monitor or monitor module therein. The monitor module frame may be a unitary piece formed by injection molding, or the monitor module frame may be constructed of two pieces of material that join together at a sealed interface. A sealing material such as acrylic or the like may then completely cover the monitor module frame and the exposed monitor screen of the monitor module. Accordingly, the sealing material provides a gas and liquid impervious encasement for the monitor module held within the monitor module frame. In one variation of this embodiment, the monitor module frame itself may be gas and liquid impervious and include an integral transparent cover forming a window portion that is positioned over the monitor screen of the monitor module. In this variation, no sealing material is required because the monitor module frame and transparent cover completely encapsulates the monitor module therein. A cable drape may be sealed to the monitor module frame enabling communication cables and the like to exit the sealed monitor module.

The monitor module frame may be sterilized by soaking it in a disinfecting solution or may be gas completely sterilized, a monitor module housed within the monitor module frame may be used a number of times without having to place the monitor module in a new monitor module frame. This sterilizable feature of the monitor module housed within the monitor module frame greatly enhances the ease in which a visual display of a surgical area can be provided within close proximity of the surgeon.

In another embodiment, a standard laptop computer may be used in conjunction with the sterile enclosure. In this embodiment, separate ports are formed on the flexible body of the sterile enclosure for enabling a vacuum to be pulled on the interior open space of the sterile enclosure covering the laptop computer and another port for handling any cables which may communicate with other video equipment within the operating room.

In yet another embodiment, at least two or more video monitors or monitor modules may be housed within a single sterile enclosure which allows a surgeon to view a number of surgical sites simultaneously or to view the same surgical site from a number of different viewpoints. Some surgical procedures may require a surgeon to have more than one view of a particular surgical area. In other circumstances, a surgeon may be conducting surgical procedures on remote locations of the patient's body. In either case, the ability for a surgeon to view separate surgical sites or the same surgical site from different viewpoints can greatly increase the safety and efficiency of the overall surgical procedure. Accordingly, this embodiment provides a sterile enclosure having a plurality of transparent covers formed on the single sterile enclosure. The screen of each monitor module may be viewed through the transparent covers.

Depending upon the type of video monitor or monitor module used, a surgeon may manipulate the image shown on the monitor screen by either touch screen controls which are activated by touching the monitor screen or by a plurality of membrane switches which are separately formed on the monitor module frame and wired so that they may control the image shown on the monitor module.

As for the first and second embodiments, again depending upon the type of video monitor or monitor module used, control of the image shown on the monitor screen may be achieved either by touch screen features or by membrane switches or keypads which are manufactured as part of the video monitor or monitor module.

In operation, the sealed video monitor or monitor module is placed directly on the patient or directly adjacent to the patient at a location in which surgery is being performed. By the use of lightweight and compact monitor modules which can be easily maintained in a sterile state by use of the sterile enclosure or sealing material, a video image of the surgical area can be provided to a surgeon in an aligned position with respect to the surgical area. This position can be along the surgeon's normal line of vision to minimize fatigue and discomfort.

Additional advantages of this invention will become apparent from the description that follows, taken in conjunction with the accompanying drawings.

BRIEF DESCRIPTION OF THE DRAWINGS

FIG. 1 is a perspective view of a first embodiment of the sterile encapsulated endoscopic video monitor of this invention;

FIG. 1a is a fragmentary vertical section, taken along line 1a of FIG. 1, illustrating the positioning of a monitor module mounted in a monitor module frame and covered by a sterile enclosure.

FIG. 2 is a fragmentary perspective view, similar to FIG. 1, showing a sterile enclosure having a transparent cover defining a window portion adapted to correspond with a particular type of monitor module;

FIG. 3 is a perspective view of a second embodiment of the sterile encapsulated endoscopic video monitor and method of this invention illustrating the monitor module frame as a unitary piece with membrane switches located thereon;

FIG. 3a is a fragmentary vertical section, taken along line 3a of FIG. 3, illustrating the relationship of the monitor module housed within the unitary piece monitor module frame;

FIG. 4 is another perspective view of the second embodiment of this invention illustrating the monitor module frame of two-piece construction with touch screen controls located on the monitor screen of the monitor module which can be activated through a sealing material covering the monitor module frame;

FIG. 4a is a fragmentary vertical section, taken along line 4a of FIG. 4, illustrating the relationship of the monitor module housed within the monitor module frame and encapsulated in the sealing material;

FIG. 5 is a perspective view of a third embodiment of the sterile encapsulated endoscopic video monitor of this invention illustrating a standard laptop computer sealed within a sterile enclosure;

FIG. 6 is a perspective view of a fourth embodiment of the sterile encapsulated endoscopic video monitor of this invention showing two independent monitor modules encapsulated within the sterile enclosure which includes a pair of transparent covers defining corresponding window portions;

FIG. 7 is a perspective view of a sterile enclosure prior to inserting a monitor module therein.

BEST MODE FOR CARRYING OUT THE INVENTION

Figure 8:
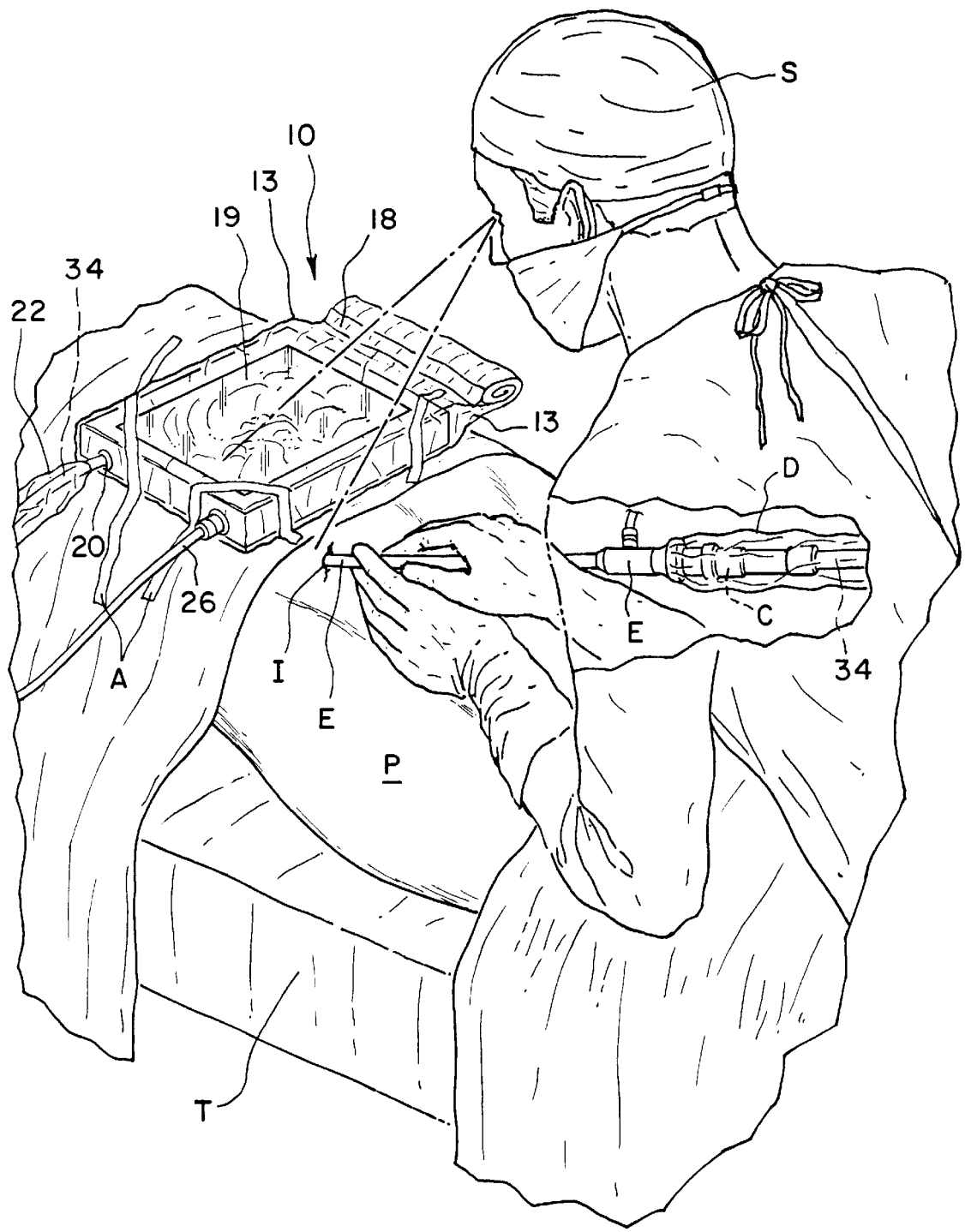
FIG. 8 is a perspective view of the sterile encapsulated endoscopic video monitor of this invention as it is being used in a surgical procedure.

According to the first embodiment as shown in FIGS. 1, 1a and 2, the sterile encapsulated endoscopic video monitor of this invention 10 includes a video monitor or monitor module 30 which is placed inside a sterile enclosure 12. The sterile enclosure 12 includes a flexible body 13 which may conform to the particular shape of the monitor module used. The sterile enclosure 12 is defined by a closed distal end 14 and an open proximal end 16 which receives a monitor module 30. An enclosure seal 18 lies adjacent the proximal end 16 to completely seal the monitor module 30 inside the sterile enclosure 12 thus isolating the monitor module 30 from the sterile field of the operating room. Enclosure seal 18 may be adhesive tape or another appropriate sealing means. In general, the sterile field of the operating room is situated around the body of the patient P. The sterile enclosure 12 may be made of a substantially transparent and liquid and gas impermeable material such as polyurethane, polyolefins, laminated plastic films or the like. Optionally, an integral transparent cover defining a window portion 19 may be formed along a cut-out portion of the flexible body 13 so that the window portion enhances the ability to view the monitor screen within the sterile enclosure 12. The window portion 19 may be made of an optically clear material such as acrylic or polycarbonate and, if desired, may be more rigid than enclosure 12. The window portion 19 is completely sealed with respect to the flexible body 13 so that contamination cannot exit the interior open space within the sterile enclosure 12 into the sterile field. A cable port 20 may be formed on the distal end 14 of the sterile enclosure 12 to accommodate the exit of a communication cable 34 which may connect to the monitor module 30. Accordingly, a cable drape 22 is provided to completely seal cable 34 from the sterile field. As shown in FIG. 1a, the monitor module 30 includes a monitor screen 32 which is positioned adjacent the window portion 19. Additionally, window portion 19 may be sized to fit the particular type of monitor screen 32 of the monitor module 30.

As shown in FIG. 2, a vacuum port 24 may be provided on the sterile enclosure 12 and placed in communication with a vacuum line 26 connected to an external source of vacuum so that the sterile enclosure may be tightly held against the monitor module 30. By drawing a vacuum upon the interior open space within the sterile enclosure 12, distortion of an image may be minimized by undulations or folds in the window portion 19. Additionally, the sterile enclosure 12 is less likely to be torn or ripped if held tightly against the monitor module.

As shown in FIG. 1a, a monitor module frame 36 may be provided to help stabilize the monitor module within the sterile enclosure 12. Oftentimes, a monitor module 30 may have a particularly sharp edge which, if exposed, may inadvertently rip or tear the sterile enclosure 12. As shown, the monitor module frame 36 may include an upper peripheral portion 37 extending around the peripheral edges of the monitor module 30 and a lower portion 38 which covers the back side of the monitor module. FIG. 2 illustrates a monitor module which does not have sharp edges that could present a danger of ripping or puncturing the sterile enclosure 12 and which is placed directly in a sterile enclosure without a monitor module frame.

According to a second embodiment of the sterile encapsulated endoscopic video monitor of this invention, as shown in FIGS. 3 and 3a, a unitary piece monitor module frame 40 is provided for housing a video monitor or monitor module 50 therein. The frame 40 includes a transparent cover defining an integral window portion 41 which is aligned with the monitor screen 54 of the monitor module 50. Monitor module 50 is encapsulated within the frame 40 during the formation of frame 40 which is achieved, for example, by injection molding then attaching and sealing the window portion 41 thereto. According to one variation of the second embodiment, as shown in FIG. 4, a clamshell type monitor module frame 40 includes an upper portion 42 and a lower portion 44 which houses the monitor module 50 therein. A sealed interface 46 defines the connection of the upper portion 42 to the lower portion 44. As best seen in FIG. 4a, monitor module 50 is completely encapsulated within a sealing material 59 such as acrylic so that the monitor module is isolated from the sterile field of the operating room. As shown, the upper portion 42 of the monitor module frame 40 has an opening which corresponds in size and shape to the monitor screen 54. Conveniently, the sealing material 59 directly contacts the monitor screen 54 and is transparent at least over the opening to permit viewing of the monitor screen 54.

As seen in FIG. 3, external membranes switches 52 may be positioned on the monitor module frame 40. These switches may be wired with the controls of the monitor module to directly control the visual images displayed on the monitor screen 54.

Alternatively, as shown in FIG. 4, touch screen switches 56 may be utilized so that control of an image on the monitor screen 54 is achieved by simply touching the sealing material 59 covering the monitor screen 54 at the appropriate location. As shown in both FIGS. 3 and 4, the monitor module may include a monitor module cable 58 which must also be isolated from the sterile field. Accordingly, a cable port 47 allows the cable 58 to exit the monitor module frame and is completely covered by cable drape 48 which is sealed against the monitor module frame 40.

Although FIGS. 3 and 4 illustrate a monitor module including a cable 58, monitor modules are manufactured which do not require external cables for power or communication and can communicate with a video camera via infrared, radio or other electromagnetic waves.

As shown in FIG. 5, in a third embodiment, the encapsulated video monitor of this invention may be in the form of a standard laptop computer 60 that is encapsulated within a sterile enclosure 12a similar to the sterile enclosure 12 of the first embodiment. As shown, the laptop computer 60 includes a laptop computer screen 62 which, when in the unfolded position, is exposed for viewing. A communications cable 64 may attach to the laptop computer 60. Sterile enclosure 12a comprises a flexible body 13a which is substantially transparent so that a surgeon may view both the keyboard and controls of the laptop computer 60 and the laptop computer screen 62. When inserted into the sterile enclosure 12a, the keyboard of the laptop computer 60 lies adjacent the closed distal end 14a of the sterile enclosure 12a. The open proximal end 16a of the sterile enclosure 12a may be appropriately sealed from the surrounding environment by rolling the distal end and then securing it to the flexible body 13a by means of tape or adhesive 18a. Cable drape 22a extends away from the sterile enclosure 12a and completely encapsulates the cable 64 therein. As with the first embodiment shown in FIG. 2, a vacuum port 24a and vacuum line 26a are provided to hold the sterile enclosure 12a tightly against the laptop computer 60.

Yet another embodiment, as shown in FIG. 6, is provided wherein a pair of side-by-side video monitors or monitor modules 30 may be placed within a single sterile enclosure 70. In some surgical procedures, it may be necessary to operate on the patient at two remote locations within the patient's body. Accordingly, it may be necessary to simultaneously view the two surgical sites. Also, it may be required to have two different views of the same surgical site which can be accommodated by viewing two monitor modules communicating with respective endoscope and camera setups. More particularly, sterile enclosure 70 includes a flexible body 72 bounded by a closed distal end 74 and open proximal end 76 which is sealed as by rolling it and sealing it to the flexible body 72 as by tape or adhesive 78. A single cable port 80 can accommodate any cables 34 from the pair of monitor modules encapsulated within the sterile enclosure 70. Accordingly, cable drape 82 attaches to flexible body 72 and covers the cable(s) 34 an appropriate length. Alternatively, as shown, a separate cable port 80 and drape 82 may be provided for each of the cables 34 of the monitor modules 30. A vacuum port 84 may be formed on the flexible body 72 in order that vacuum line 86 can communicate with a source of vacuum (not shown) so that a vacuum may be drawn on interior open space within the sterile enclosure 70. A first window portion 87 is aligned with the monitor screen of one of the monitor modules encapsulated within the sterile enclosure 70 and a second window portion 88 aligns with the other monitor module screen.

The use of the sterile encapsulated endoscopic video monitor 10 can best be seen in FIGS. 7 and 8. Prior to inserting a video monitor or monitor module within the sterile enclosure 12, the sterile enclosure 12 comes configured such that the open proximal end 16 includes a cuff portion 28 comprising a plurality of accordion folds 29. In order to ensure that sterility is maintained while inserting the unsterile monitor module within the sterile enclosure 12, a sterile nurse will position his/her hands between the flexible body 13 and the first fold of accordion folds 29. Then another nurse will place the monitor module within the sterile enclosure 12 by first routing any monitor module cables 34 through the cable port 20 and into the cable drape 22, and then continue to move the monitor module 30 so that it is entirely encapsulated within the sterile enclosure 12. Next, the sterile nurse will unfold the accordion folds 29 located at the open proximal end 16 of the sterile enclosure 12 and will roll fold the open proximal end 16 in order to isolate the monitor module from the outside environment. An appropriate tape or adhesive 18 may be placed over the rolled distal end of the sterile enclosure 12 providing an enclosure seal. As shown in FIG. 8, once the monitor module is encapsulated within the sterile enclosure, the video monitor may be placed on or adjacent to a patient P as by adhesive tape A or an appropriate support stand (not shown) in a visually aligned position with respect to the surgeon's line of vision and the surgical area(s) or site(s). A drape D is placed over the proximal end of the endoscope and over the video camera C which connects to the endoscope E. Video signals are sent directly to the video monitor via monitor cable 34. In the surgical procedure being conducted, the surgeon S is standing toward the foot of the operating table T and observes the video monitor 10 in a visually aligned position with respect to the endoscope E which is inserted into the incision I. Because of the proximity of the video monitor 10 with respect to both the surgeon S and the surgical site, the surgeon may manipulate the image produced on the video monitor 10 without having to turn away from the surgical site or by having another operating room person adjust the image for the surgeon. The sterile field is properly protected from contamination by use of the sterile enclosure 12 which is placed over the monitor module 30.

In accordance with the invention and method described above, numerous problems associated with the use of video equipment in endoscopic procedures can be overcome. Since the sterile encapsulated endoscopic video monitor provides a means by which a surgeon may conveniently position a video image of the surgical site in visual alignment with the surgical area, the surgeon's ability to properly manipulate an endoscope is greatly enhanced. Also, surgeon fatigue will be minimized by preventing the surgeon from conducting a surgical procedure in a strained position. That is, since the surgeon does not have to look away from the surgical area to view the monitor module, the surgeon may be in a more natural position.

Since the monitor module contained within the sterile enclosure is small and lightweight, and also has integral switches for controlling the type of image viewed, the surgeon may easily adjust the type of image to be viewed as well as position the monitor module with a minimum amount of disruption during a surgical procedure. By the use of the sterile enclosure which completely encloses the monitor module and any associated cables, the encapsulated video monitor may be placed within the sterile field of the operating room; however, sterility is not sacrificed at the cost of achieving improved imaging of the surgical area.

If the surgeon is required to make an additional incision and operate on the patient at another surgical area, the encapsulated endoscopic video monitor may be easily moved to a new location and be visually aligned.

This invention has been described in detail with reference to particular embodiments thereof, but it will be understood that various other modifications can be effected within the spirit and scope of this invention.

What is claimed is:

1. A sterile encapsulated endoscopic video monitor comprising:

a video monitor including a viewing screen in order to view a surgical site;

a frame enclosing a portion of said video monitor, said frame including an opening enabling viewing of said viewing screen of said monitor; and a sterile enclosure made of a flexible material substantially impervious to liquid and gas, and an inner surface defining an interior open space for encapsulating said video monitor and said frame therein.

2. An apparatus, as claimed in claim 1, further including:

a vacuum port formed on said sterile enclosure; and means for drawing a vacuum communicating with said vacuum port enabling air to be selectively removed from the interior open space of said sterile enclosure.

3. An apparatus, as claimed in claim 2, further including:

a cable drape connected to said sterile enclosure and extending away therefrom for encapsulating a communication cable of said video monitor.

4. A sterile encapsulated endoscopic video monitor comprising:

a video monitor including a viewing screen in order to view a surgical site;

a sterile enclosure including a body portion made of a material substantially impervious to liquid and gas, and an inner surface defining an interior open space for encapsulating said video monitor therein;

a vacuum port formed on said body portion of said sterile enclosure;

a vacuum line connected to said vacuum port in sealing engagement thereto enabling air to be removed from the interior open space of said sterile enclosure; and a frame enclosing said video monitor, said frame including an opening enabling viewing of said viewing screen of said video monitor and wherein said sterile enclosure encapsulates said video monitor which is enclosed within said frame.

5. An apparatus, as claimed in claim 4, further including:

a cable drape connected to said sterile enclosure and extending away therefrom for encapsulating a communication cable of said video monitor.

6. An apparatus, as claimed in claim 4, wherein said sterile enclosure is made of a flexible material.

7. An apparatus, as claimed in claim 4, wherein:

said sterile enclosure further includes an opening formed on said body portion, said sterile enclosure further including a transparent cover placed over said opening in sealing engagement with said body portion and alignable with said viewing screen of said video monitor.

8. A sterile encapsulated endoscopic video monitor comprising:

a video monitor including a viewing screen in order to view a surgical site;

means for enclosing said video monitor, said enclosing means including an inner surface defining an interior open space and wherein said video monitor is controllably sealed within the interior open space of said enclosing means;

a vacuum port formed on said enclosing means;

means for drawing a vacuum communicating with said vacuum port enabling air to be selectively removed from the interior open space of said enclosing means; and a frame enclosing said video monitor, said frame including an opening enabling viewing of said viewing screen of said video monitor and wherein said sterile enclosure encapsulates said video monitor which is enclosed within said frame.

9. An apparatus, as claimed in claim 8, further including:

means for covering a communication cable attached to said video monitor, said covering means being sealably connected to said enclosing means and extending away therefrom and over said communication cable.

10. An apparatus, as claimed in claim 8, wherein:

said enclosing means includes a flexible body portion, an opening formed on said flexible body portion and a transparent cover placed over said opening and in sealing engagement with said body portion and alignable with said viewing screen of said viewing monitor.

11. Sterile encapsulated endoscopic video monitors for viewing a plurality of surgical sites or to view one particular site from different viewpoints, said video monitors comprising:

at least two video monitors each including a video screen;

a sterile enclosure including a body portion made of a material substantially impervious to liquid and gas, an inner surface defining an interior space for enclosing said at least two video monitors therein;

at least one transparent cover positioned over and in sealing engagement with said body portion, said at least one transparent cover being positionable in alignment with said viewing screens of said at least two video monitors in order that a surgeon may view both said viewing screens through said at least one transparent cover;

a vacuum port formed on said body portion of said sterile enclosure;

a vacuum line connected to said vacuum port in sealing engagement thereto enabling air to be removed from the interior open space of said sterile enclosure; and at least one cable drape connected to said sterile enclosure and extending away therefrom for encapsulating a communication cable from each of said at least two video monitors.

* * * * *